United States Patent [19]
Paul

[11] Patent Number: 5,527,297
[45] Date of Patent: Jun. 18, 1996

[54] SYRINGE SPLASH GUARD

[76] Inventor: Marlene L. Paul, 2635 Fifth St., Slidell, La. 70459

[21] Appl. No.: 354,611

[22] Filed: Dec. 13, 1994

[51] Int. Cl.⁶ .................................................... A61M 5/32
[52] U.S. Cl. ................................... 604/263; 604/192
[58] Field of Search ................................... 604/198, 187, 604/192, 263, 110

[56] References Cited

U.S. PATENT DOCUMENTS

| | | | |
|---|---|---|---|
| 3,134,380 | 5/1964 | Armao | 604/198 |
| 4,737,144 | 4/1988 | Choksi | 604/198 |
| 4,775,369 | 10/1988 | Schwartz | 604/263 |
| 4,795,432 | 1/1989 | Karczmer | 604/110 |
| 4,915,697 | 4/1990 | DuPont | 604/192 |
| 5,163,908 | 11/1992 | Lambert | 604/110 |

*Primary Examiner*—John D. Yasko
*Attorney, Agent, or Firm*—Joseph N. Breaux

[57] ABSTRACT

A syringe splash guard including a shield member; and an attachment member, in connection with the shield member, having a mechanism for securing the shield member to a syringe. The shield member includes a resilient accordion structure that is collapsible when pressed against the skin surface of a patient allowing the hypodermic needle to be easily inserted through the skin of a patient. As the needle is withdrawn, the end of the shield member resiliently returns toward a fully extended position covering the insertion site. In a preferred embodiment, the mechanism for securing the shield member to a syringe includes a flexible band member having an adhesive coating on a surface thereof. The adhesive coating is preferably covered with a non-stick sheeting, in the manner of a self-adhesive bandage, which can be easily removed to expose the adhesive when it is desired to attach the splash guard to a syringe.

4 Claims, 2 Drawing Sheets

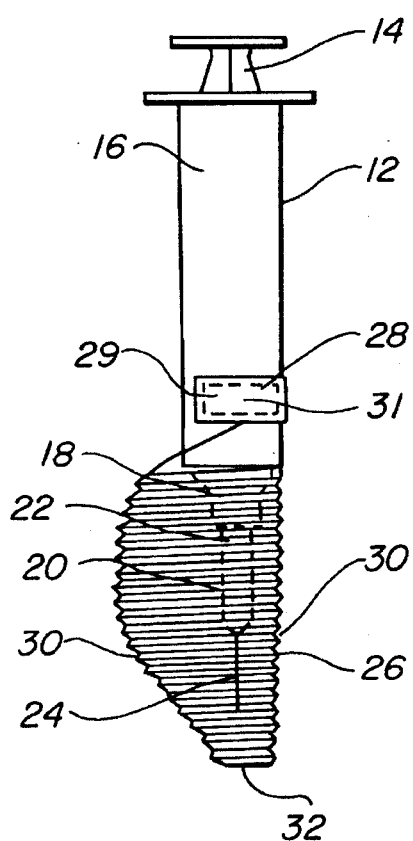
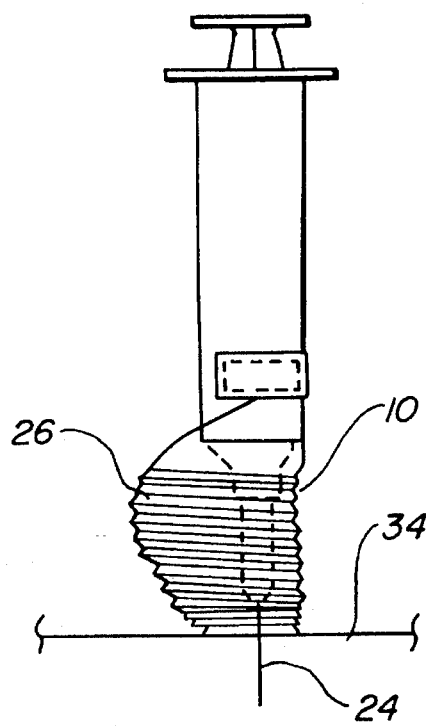
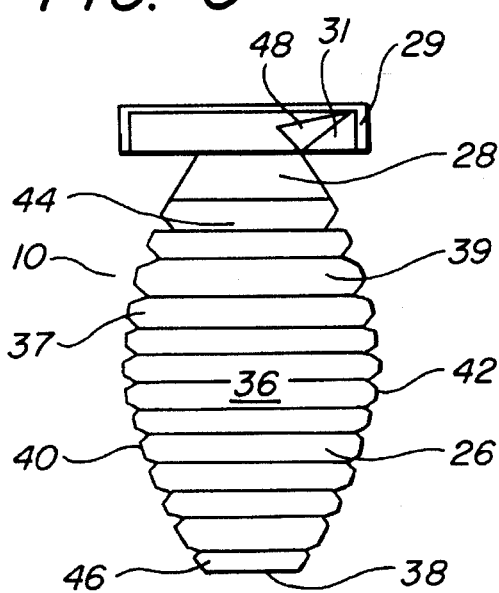
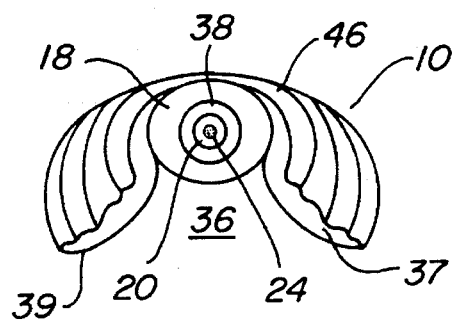

SYRINGE SPLASH GUARD

TECHNICAL FIELD

The present invention relates to devices for preventing bodily fluids from splashing on health-care workers and more particularly to devices for preventing bodily fluids from splashing on health-care workers that include a collapsible shield member.

BACKGROUND ART

Controlling the spread of diseases within a health care environment, such as a hospital or clinic, requires constant vigilance. Contagion removal, such as washing the hands with agents that kill disease spreading contagions, is one widely used method of preventing the spread of disease. Another widely used method of preventing the spread of disease includes shielding the health care provider from the disease contagions through the use of gloves, masks, goggles and shielding garments.

The shielding method is preferred when attempting to prevent the spread of such deadly diseases as acquired immune deficiency syndrome (AIDS). During the ordinary course of providing health care to patients, health care workers are placed at risk of contacting blood and other bodily fluids when performing routine health care services such as drawing blood samples and giving injections. In addition, used hypodermic needles, which can carry small amounts of contagion carrying blood, also pose the risk of sticking and infecting health care workers. Because AIDS can be spread by contact with the blood of a person infected with the disease, health care providers are routinely at risk of exposure to the disease. It would be a benefit, therefore, if a device were available which shielded health care workers from exposure to patient blood when routine procedures such as injections and blood tests were performed. It would be a further benefit if the device was inexpensive, disposable, covered the hypodermic needle both before and after the hypodermic needle was used, covered the insertion site of the hypodermic needle for a period before and after the hypodermic was inserted into and withdrawn from a patient, and was usable in conjunction with a variety of syringes and blood drawing devices.

Below is a list of U.S. Patents which are exemplary of attempts to provide such a device.

| U.S. Patent No. | Inventor |
| --- | --- |
| 5,322,516 | Brugger |
| 5,312,368 | Haynes |
| 4,898,588 | Roberts |
| D-307,474 | Cook |

U.S. Pat. No. 5,322,516, to Brugger discloses a safety needle system and method for using the same including a needle apparatus and an access site assembly for use in delivering and withdrawing fluids from a patient in a safe and effective manner.

U.S. Pat. No. 5,312,368, to Haynes discloses a shield for protecting the needle of a syringe. The shield has a connector for connecting the shield to the syringe with the connector preferably being generally annular and adapted to fit over the base of the needle. The shield includes at least one protective arm hingedly mounted upon the connector and pivotal between first and second positions. The first position is the normal position wherein the protective arm conceals the needle and the second position corresponds to the protective arm being pivotally displaced to expose the needle.

U.S. Pat. No. 4,898,588, to Roberts discloses a hypodermic syringe splatter shield for preventing high-angle back splatter, from syringe lavage, into the user's face. The splatter shield comprises a preferable circular sheet of stiff material which is preferably colorless and transparent, having a central tube which is attached thereto and which passes through the center of the sheet and projects on at least one side of the sheet sufficiently to have one end adapted to receive a standard hypodermic needle.

U.S. Design Patent U.S. Pat. No. 307,474, to Cook discloses a syringe shield having a tubular passageway therethrough. One end being flared and having an aperture through the sidewall thereof. The other end being tapered.

None of the above described devices satisfactorily provide the above described desirable features.

GENERAL SUMMARY DISCUSSION OF INVENTION

It is thus an object of the invention to provide a syringe splash guard that inexpensive.

It is a further object of the invention to provide a syringe splash guard that attachable to a variety of syringes.

It is a still further object of the invention to provide a syringe splash guard that disposable.

It is a still further object of the invention to provide a syringe splash guard that will cover the injection site during withdrawal of the needle.

Accordingly, a syringe splash guard is provided. The syringe splash guard includes a shield member; and an attachment member, in connection with the shield member, having a mechanism for securing the shield member to a syringe.

When attached to a syringe having a hypodermic needle, the shield extends out past the hypodermic needle and shields the health care provider from inadvertent punctures from the hypodermic needle. The shield member includes a resilient accordion structure that is collapsible when pressed against the skin surface of a patient allowing the hypodermic needle to be easily inserted through the skin of a patient. As the needle is withdrawn, %he end of the shield member resiliently returns toward a gully extended position coveting the insertion site. Covering the insertion site prevents fluids, which may contain disease spreading contaminants, from spurting from the insertion site onto the health care provider when the hypodermic needle is removed.

Although the the shield member may be secured to a syringe or other medical equipment in a variety of manners, such as through the use of a clip or a strap, in a preferred embodiment, the mechanism for securing the shield member to a syringe includes a flexible band member having an adhesive coating on a surface thereof. The adhesive coating is preferably covered with a non-stick sheeting, in the manner of a self-adhesive bandage, which can be easily removed to expose the adhesive when it is desired to attach the splash guard to a syringe.

The shield member is preferably constructed from a clear, resilient, plastic material in a substantially shell-shaped configuration, open along a longitudinal side and defining a shell-shaped cavity.

In a preferred embodiment, the syringe splash guard comprises: a shield member and an attachment member. The shield member has a first and second end and a plurality of accordion-type pleat structures between the first and second end. The first end at least partially defines an aperture. The accordion-type pleat structures are collapsible when the first end is pressed against the skin surface of a patient and resiliently return to a first position when the force is removed. The attachment member is in connection with the shield member and includes a mechanism for securing the shield member to a syringe.

In a preferred embodiment, the mechanism for securing the shield member to a syringe includes a band member having an adhesive coating on a surface thereof.

In another preferred embodiment, the syringe splash guard comprises: a shield member having a first and second end, the first end at least partially defining an aperture; and an attachment member, in connection with the shield member, having a means for securing the shield member about a needle end of a syringe in a manner such that a longitudinal axis of a hypodermic needle protruding from the needle end of the syringe is oriented along a line passing through a portion of the aperture partially defined by the first end. The shield member preferably has an accordion structure that is collapsible when the first end is pressed against the skin surface of a patient and resiliently returning to a first position when the force is removed from the first end.

In other preferred embodiments, the shield member is open along a longitudinal side thereof; the shield member is transparent along at least a section thereof; the mechanism for securing the shield member includes a band member having an adhesive coating on a surface thereof; the shield member defines a substantially shell-shaped cavity; and/or the shield member and the attachment member are integrally formed.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein:

FIG. 1 is a side view of an exemplary embodiment of the syringe splash guard of the present invention attached to a representative syringe with an embodiment of the shield member in the fully extended position.

FIG. 2 is a side view of the exemplary embodiment of the syringe splash guard of FIG. 1 with the shield member in a partially collapsed position.

FIG. 3 is an interior view of the embodiment of the syringe splash guard of FIG. 1 unattached to a syringe showing the syringe cavity.

FIG. 4 is an end view of the embodiment of the syringe splash guard of FIG. 1 from the aperture end showing the aperture, the needle end of the syringe, and the point of the hypodermic needle.

EXEMPLARY MODE FOR CARRYING OUT THE INVENTION

Figure 5:
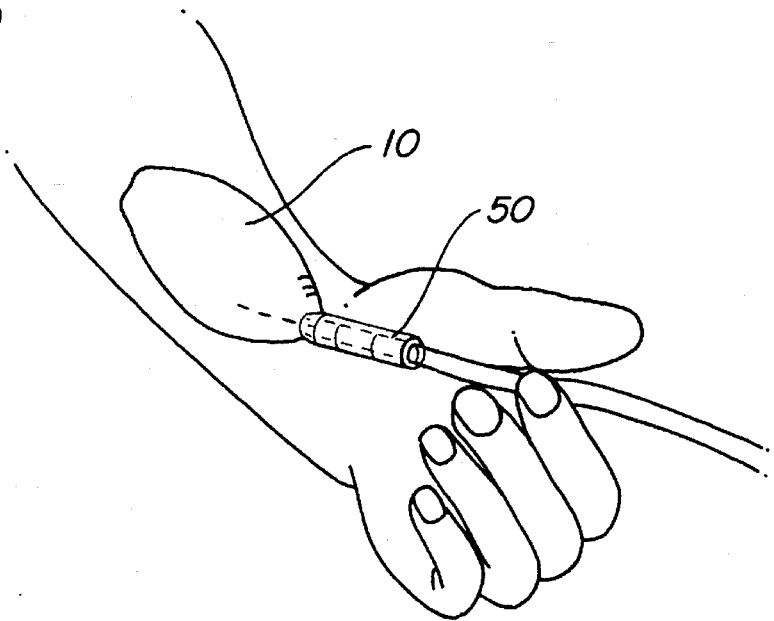
FIG. 5 is a top view of the embodiment of the syringe splash guard of FIG. 1 in use with a representative I.V. line.

FIG. 1 is a side view of an exemplary embodiment of the syringe splash guard of the present invention, generally designated by the numeral 10, attached to a representative syringe, generally designated by the numeral 12.

Syringe 12 includes a plunger 14; an outer housing 16, having a needle connection end 18; and a hypodermic needle assembly 20, having an attachment fitting 22 and a hypodermic needle 24.

Splash guard 10 is about two inches long and includes a shield member 26 and an attachment member 28. In this exemplary embodiment, shield member 26 and attachment member 28 are integrally formed from transparent, resilient plastic.

Shield member 26 includes a plurality of accordion type pleats 30 which collapse when a force is applied to an end 32 of shield member 26 and which return to their original position when the force is removed. In this embodiment each pleat 30 is about one-sixteenth of an inch deep.

Attachment member 28 includes a flexible band 29 having an adhesive coating 31 on the side in contact with outer housing 16. FIG. 2 is a side view of splash guard 10 with shield member 26 in a partially collapsed position and hypodermic needle 24 inserted into the flesh 34 of a patient.

FIG. 3 is an interior view of syringe splash guard 10 showing a syringe cavity 36, flexible band 29, and needle aperture 38. As shown in the figure, shield member 26 forms a syringe cavity 36, bounded along two sides 37, 39 by the longitudinal edges 40, 42 of shield member 26 and at one end 44, by attachment member 28. The other end 46 of syringe cavity 36 forms needle aperture 38.

Flexible band 29 is more clearly shown in the figure, and includes adhesive coating 31 and a section non-stick tape 48 covering adhesive coating 31. In use, nonstick tape 48 is removed prior to attaching syringe splash guard 10 to a syringe.

FIG. 4 is an end view of syringe splash guard 10 more clearly showing aperture 38, and the positioning of needle connection end 18 and hypodermic needle assembly 20, including hypodermic needle 24, within syringe cavity 36.

Use of syringe splash guard 10 is now described with reference to FIGS. 1–4. Syringe splash guard 10 is attached to a syringe 12 in the following manner: nonstick tape 48 is removed from adhesive coating 31 and band 29 placed about the exterior of outer housing 16 in a manner such that needle connecting end 18 and hypodermic needle 24 are entirely within syringe cavity 36. Syringe 12 is then used in the normal fashion with the exception that syringe 12 is oriented in a manner such that shield member 26 is positioned between the health care provider and the insertion site of hypodermic needle 24. Because shield member 26 includes resiliently collapsible accordion type pleats 30, end 32 of shield member 26 is forced back, as end 32 contacts the skin surface of the patient, allowing hypodermic needle 24 to pass through aperture 38 and into the patient. As hypodermic needle 24 is withdrawn from the patient, resilient pleats 30 begin to resume their original shape and force end 32 of shield member 26 to remain in contact with the skin surface of the patient until after hypodermic needle 24 has been fully withdrawn. This additional contact by end 32 with the skin surface of the patient allows shield member 26 to cover the insertion site of hypodermic needle 24 during the period of time when the risk of fluid spouting from the site is highest.

Once the injection or sample collection has been performed, syringe 12 and syringe splash guard 10 may disposed of together or syringe splash guard 10 may be detached from syringe 12 and disposed of separately.

Figure 6:
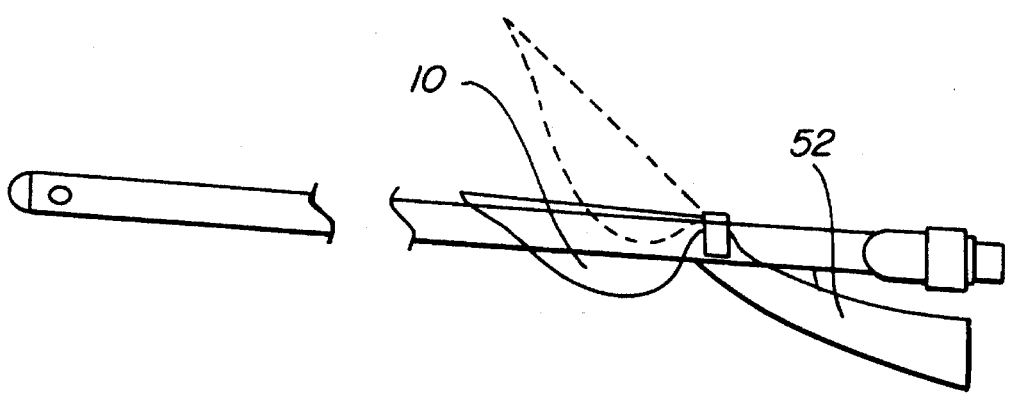
FIG. 6 is a side view of the embodiment of the syringe splash guard of FIG. 1 in use with a catheter.

As shown in FIGS. 5 and 6, syringe splash guard 10 may be used with a variety of medical equipment. FIG. 5 shows syringe splash guard 10 in use with a representative I.V. line 50. FIG. 6 shows syringe splash guard 10 in use with a catheter 52. In addition, FIG. 6 shows syringe splash guard 10 in a deflected position.

It can be seen from the preceding description that a device for preventing bodily fluids from splashing on health-care workers which is inexpensive, which is attachable to a variety of syringe types, which is disposable, and which covers the injection site during withdrawal of the needle has been provided.

It is noted that the embodiment of the syringe splash guard described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A syringe splash guard comprising:

shield member; and an attachment member in connection with said shield member, having means for securing said shield member to a syringe;

said shield member including an accordion structure that is collapsible when pressed against the skin surface of a patient and resiliently returns to a first position when said force is removed, and defining a substantially shell-shaped cavity.

2. A syringe splash guard comprising:

a shield member having a first and second end and a plurality of accordion-type pleat structures between said first and second end, said first end at least partially defining an aperture, said accordion-type pleat structures being collapsible when said first end is pressed against the skin surface of a patient and resiliently returning to a first position when said force is removed; and an attachment member, in connection with said shield member, including means for securing said shield member to a syringe;

said shield member defining a substantially shell-shaped cavity.

3. A syringe splash guard comprising:

a shield member having a first and second end, said first end at least partially defining an aperture; and an attachment member, in connection with said shield member, having a means for securing said shield member about a needle end of a syringe in a manner such that a longitudinal axis of a hypodermic needle protruding from said needle end of said syringe is oriented along a line passing through a portion of said aperture partially defined by said first end;

said shield member having an accordion structure that is collapsible when said first end is pressed against the skin surface of a patient and resiliently returning to a first position when said force is removed from said first end, said means for securing said shield member includes a band member having an adhesive coating on a surface thereof, said shield member being transparent along a section thereof, said shield member defining a substantially shell-shaped cavity.

4. The syringe splash guard of claim 3 wherein: said shield member is open along a longitudinal side thereof.

* * * * *